United States Patent
Antoni-Zimmermann et al.

(10) Patent No.: US 8,323,674 B2
(45) Date of Patent: *Dec. 4, 2012

(54) SYNERGISTIC BIOCIDE COMPOSITION COMPRISING 2-METHYLISOTHIAZOLINE-3-ONE

(75) Inventors: Dagmar Antoni-Zimmermann, Speyer (DE); Rudiger Baum, Waghausel (DE); Hans-Jurgen Schmidt, Speyer (DE); Thomas Wunder, Neustadt/Weinstrasse (DE)

(73) Assignee: Thor GmbH, Speyer (DE)

(*) Notice: Subject to any disclaimer, the term of this patent is extended or adjusted under 35 U.S.C. 154(b) by 671 days.

This patent is subject to a terminal disclaimer.

(21) Appl. No.: 12/319,828

(22) Filed: Jan. 12, 2009

(65) Prior Publication Data

US 2009/0156570 A1 Jun. 18, 2009

Related U.S. Application Data

(62) Division of application No. 10/362,326, filed as application No. PCT/EP01/05939 on May 23, 2001, now abandoned.

(30) Foreign Application Priority Data

Aug. 31, 2000 (DE) .................. 100 42 894

(51) Int. Cl.
*A01N 25/32* (2006.01)
*A01N 43/80* (2006.01)
*A01N 33/18* (2006.01)
*A61K 31/74* (2006.01)
*A61K 31/155* (2006.01)
*A61K 31/115* (2006.01)

(52) U.S. Cl. ............ 424/406; 424/78.08; 514/372; 514/635; 514/697; 514/727

(58) Field of Classification Search ......... 424/78.08, 424/406; 514/372, 635, 697, 727
See application file for complete search history.

(56) References Cited

U.S. PATENT DOCUMENTS

| | | | |
|---|---|---|---|
| 5,125,967 A * | 6/1992 | Morpeth et al. | 106/18.22 |
| 5,328,926 A | 7/1994 | Oppong | |
| 5,466,818 A | 11/1995 | Petigara | |
| 5,716,628 A * | 2/1998 | Vinopal et al. | 424/405 |
| 6,846,777 B2 * | 1/2005 | Antoni-Zimmermann et al. | 504/126 |

FOREIGN PATENT DOCUMENTS

EP 0 676 140 A1 10/1995

* cited by examiner

*Primary Examiner* — Blessing Fubara
(74) *Attorney, Agent, or Firm* — Hedman & Costigan, P.C.; James V. Costigan

(57) ABSTRACT

A biocide composition, comprising 2-methylisothiazolin-3-one as a biocidal active ingredient and at least one further biocidal active ingredient, as an additive to materials capable of being attacked by harmful microorganisms, wherein the composition comprises a pyrithione as the further biocidal active ingredient.

12 Claims, No Drawings

SYNERGISTIC BIOCIDE COMPOSITION COMPRISING 2-METHYLISOTHIAZOLINE-3-ONE

This application is a division of Ser. No. 10/362,326, filed Feb. 20, 2003 which claims the priority of PCT/EP01/05939, filed May 23, 2001, which claims the priority of German application Serial No. 100 42 894.0, filed Aug. 31, 2000.

The invention relates to a biocide composition, comprising 2-methylisothiazolin-3-one as biocidal active ingredient (MIT), and at least one further biocidal active ingredient, as additive to materials capable of being attacked by harmful microorganisms.

Biocidal agents are employed in many fields, for example in the control of harmful bacteria, fungi and algae. It has long been known to employ, in such compositions, 4-isothiazolin-3-ones (also termed 3-isothiazolones), since this group contains potent biocidal compounds.

One of these compounds is 5-chloro-2-methylisothiazolin-3-one. While it has a good biocidal action, it has various disadvantages on handling in practice. For example, the compound frequently triggers allergies in people handling it. Also, some countries have legal limits for the AOX value of industrial waste-water, i.e. a certain concentration of organochlorine, organobromine and organoiodine compounds which are adsorbable to active charcoal must not be exceeded in the water. This prevents 5-chloro-2-methyl-isothiazolin-3-one from being used as much as would be desirable. Moreover, the stability of this compound is insufficient under certain conditions, for example at high pH values or in the presence of nucleophiles or reducing agents.

Another biocidally active, known isothiazolin-3-one is 2-methylisothiazolin-3-one. While the compound avoids the various disadvantages of 5-chloro-2-methylisothiazolin-3-one, for example the high risk of allergy, it is substantially less biocidally active. A simple exchange of 5-chloro-2-methyl-isothiazolin-3-one by 2-methylisothiazolin-3-one is therefore not possible.

Also, it is already known to use combinations of various isothiazolin-3-ones or combinations of at least one isothiazolin-3-one and other compounds. For example, EP 0676140 A1 describes a synergistic biocidal composition comprising 2-methylisothiazolin-3-one (2-methyl-3-isothiazol-one) and 2-n-octylisothiazolin-3-one (2-n-octyl-3-isothiazol-one).

U.S. Pat. No. 5,328,926 discloses synergistic biocide compositions which are combinations of 1,2-benzoisothiazolin-3-one (BIT) and an iodopropargyl compound (iodopropynyl compound). For example, 3-iodopropargyl-N-butylcarbamate is mentioned as one such compound.

The invention is based on the object of indicating a biocide composition which is substantially free from 5-chloro-2-methylisothiazolin-3-one, i.e. in which the weight ratio of MIT to 5-chloro-2-methylisothiazolin-3-one is at least 100:1. Moreover, the components of the biocide composition are intended to act synergistically so that, when employed simultaneously, they can be used in lower concentrations compared with the concentrations required in the case of the individual components. This is intended to be less damaging to humans and the environment and to reduce the costs of controlling harmful microorganisms.

This object is achieved by the invention by a biocide composition of the type mentioned at the outset, which comprises, as further biocidal active ingredient, formaldehyde (HCHO) or a formaldehyde-releasing substance, 2-bromo-2-nitro-1,3-propanediol (bronopol, BNP), polyhexamethylenebiguanide (PMG), o-phenylphenol (OPP), a pyrithione, preferably zinc pyrithione (ZnPy), sodium pyrithione (NaPy), copper pyrithione (CuPy) and iron pyrithione (FePy), N-butyl-1,2-benzoisothiazolin-3-one (BBIT), N-hydroxymethyl-1,2-benzoisothiazolin-3-one (HMBIT) and/or a benzalkonium chloride, preferably dimethylbenzylalkonium chloride (BAC). These further biocidal active ingredients can be present, in the biocide composition, in each case individually or in a combination of at least two of them, in addition to the MIT.

The biocide composition according to the invention is distinguished, inter alia, by the fact that the combination of MIT and one of the above-mentioned further biocidal active ingredients act synergistically and can therefore be used with a lower overall concentration of the biocidal components.

The biocide composition according to the invention has the advantage that it can replace active ingredients which have previously been used in practice, but which are disadvantageous with regard to health and the environment, for example 5-chloro-2-methylisothiazolin-3-one. Moreover, if required, the biocide composition according to the invention can be prepared using only water as advantageous medium. Furthermore, the invention allows the composition to be adapted to specific uses by adding further active ingredients, for example with regard to an improved biocidal action, an improved long-term protection of the materials attacked by microorganisms, better compatibility with the materials to be protected, or an improved toxicological or ecotoxicological behavior.

The biocide composition according to the invention normally comprises the MIT and the above-mentioned further biocidal active ingredient in a weight ratio of from 1:100 to 100:1, preferably in the weight ratio of from 1:20 to 10:1.

The MIT and the above-mentioned further biocidal active ingredient are present, in the biocide composition, in an overall concentration of, preferably, 0.1 to 100% by weight, in particular 1 to 50% by weight, very especially preferably 1 to 20% by weight, in each case based on the entire biocide composition.

It is expedient to employ the biocides of the composition according to the invention in combination with a polar or unpolar liquid medium. In this context, this medium may, for example, already exist in the biocide composition and/or in the material to be preserved.

Preferred polar liquid media are water, an alcohol, such as an aliphatic alcohol having 1 to 4 carbon atoms, for example ethanol and isopropanol, an ester, a glycol, for example ethylene glycol, diethylene glycol, 1,2-propylene glycol, dipropylene glycol and tripropylene glycol, a glycol ether, for example butyl glycol and butyl diglycol, a glycol ester, for example butyl diglycol acetate or 2,2,4-trimethylpentanediol monoisobutyrate, a polyethylene glycol, a polypropylene glycol, N,N-dimethylformamide or a mixture of such materials.

For example, aromatics, preferably xylene, toluene and alkylbenzols, and paraffins, unpolar esters, such as phthalates and fatty acid esters, epoxidized fatty acids and their derivatives, and silicone oils serve as unpolar liquid media.

The biocide composition according to the invention may also be combined simultaneously with a polar and an unpolar liquid medium.

In addition to MIT and the above-mentioned further biocidal active ingredients, the biocide composition according to the invention may additionally comprise one or more additional biocidal active ingredients which are selected to suit the field of application. Specific examples of such additional biocidal active ingredients are given hereinbelow.

Benzyl alcohol
2,4-Dichlorobenzyl alcohol
2-Phenoxyethanol
2-Phenoxyethanol hemiformal
Phenylethyl alcohol
5-Bromo-5-nitro-1,3-dioxane
Dimethyloldimethylhydantoin
Glyoxal
Glutardialdehyde
Sorbic acid
Benzoic acid Salicylic acid
p-Hydroxybenzoic esters
Chloroacetamide
N-Methylolchloroacetamide
Phenols such as p-chloro-m-cresol
N-Methylolurea
N,N'-Dimethylolurea
Benzyl formal
4,4-Dimethyl-1,3-oxazolidine
1,3,5-Hexahydrotriazine derivatives
Quaternary ammonium compounds such as
N-alkyl-N,N-dimethylbenzylammonium chloride and
di-n-decyldimethylammonium chloride
Cetylpyridinium chloride
Diguanidine
Chlorohexidine
1,2-Dibromo-2,4-dicyanobutane
3,5-Dichloro-4-hydroxybenzaldehyde
Ethylene glycol hemiformal
Tetra(hydroxymethyl)phosphonium salts
Dichlorophene
2,2-Dibromo-3-nitrilopropionamide
3-Iodo-2-propynyl-N-butylcarbamate
Methyl N-benzimidazol-2-ylcarbamate
2-n-Octylisothiazolin-3-one
4,5-Dichloro-2-n-octylisothiazolin-3-one
4,5-Trimethylene-2-methylisothiazolin-3-one
Di-N-methyl-2,2'-dithiodibenzamide
2-Thiocyanomethylthiobenzothiazole
C-Formals, such as
2-hydroxymethyl-2-nitro-1,3-propanediol
Methylene bisthiocyanate
Reaction products of allantoin with formaldehyde.

In addition, the biocide composition according to the invention may comprise other customary constituents which are known as additives to the skilled worker in the biocides field. Examples of these are thickeners, antifoams, pH regulators and stabilizers, perfumes, dispersants, coloring matter and stabilizers against discoloration, for example complexing agents, and against the degradation of active ingredient.

MIT is a known compound and can be prepared, for example, as described in U.S. Pat. No. 5,466,818. The reaction product obtained can be purified for example by column chromatography.

HCHO, as is known, is widely available commercially.

BNP is commercially available, for example, from BASF AG, under the trade name "Myacide® AS".

PMG is available from Avecia under the trade name "Vantocil IB".

OPP is available from Bayer under the trade name "Preventol O extra".

Pyrithiones are available from Arch Chemicals, for example ZnPy under the trade name "Zinc-Omadine" and NaPy under the trade name "Natrium-Omadine". CuPy and FePy can be obtained by known methods by reacting NaPy with copper salts or iron salts, respectively.

BBIT is available from Avecia under the trade name "Vanquish 100".

HMBIT can be obtained by crystallizing a reaction mixture of formaldehyde and BIT.

BAC is available from Thor GmbH under the trade name "BAC 50".

The biocide composition according to the invention can be employed in very different fields. For example, it is suitable for use in paints, renderings, lignosulfonates, chalk suspensions, glues, photochemicals, casein-containing products, starch-containing products, bitumen emulsions, surfactant solutions, fuels, cleaners, cosmetic products, water circuits, polymer dispersions and cooling lubricants against attack by, for example, bacteria, filamentous fungi, yeasts and algae.

In these materials to be preserved, the biocides are generally employed in an overall concentration in the range of from 1 to 100 000 ppm, preferably 10 to 10 000 ppm, based on all of the material to be preserved.

When used in practice, the biocide composition can be introduced either as a ready mix or by separately adding the biocides and the optional remaining components of the composition to the material which is to be preserved.

The examples illustrate the invention.

EXAMPLE 1

This example demonstrates the synergism of the combinations of MIT and HCHO in the biocide composition according to the invention.

To this end, aqueous mixtures with different concentrations of MIT and HCHO were prepared, and the effect of these mixtures on *Pseudomonas aeruginosa* was tested.

In addition to the biocide component and water, the aqueous mixtures also comprised a nutrient medium, viz. a commercially available Müller-Hinton broth. The cell density was $10^6$ cells/ml. The incubation time was 96 hours at 25° C. Each sample was incubated in a shaker-incubator at 120 rpm.

Table I hereinbelow shows the concentrations of MIT and HCHO used. It can also be seen from this table whether microbial growth took place (symbol "+") or not (symbol "−").

Thus, table I also shows the minimum inhibitory concentrations (MICs). Accordingly, an MIC value of 60 ppm results when only MIT is used, and an MIC value of 100 ppm when only HCHO is used. In contrast, the MIC values of mixtures of MIT and HCHO are markedly lower, that is to say the combination of MIT and HCHO acts synergistically.

TABLE I

*Pseudomonas aeruginosa*: MIC values of MIT + HCHO at an incubation time of 96 h/25° C.

| MIT concentration (ppm) | HCHO concentration (ppm) | | | | | | | | | | |
|---|---|---|---|---|---|---|---|---|---|---|---|
| | 3 | 2 | 1 | 0.75 | 0.5 | 0.4 | 0.3 | 0.2 | 0.1 | 0.05 | 0 |
| 100 | − | − | − | − | − | − | − | − | − | − | − |
| 80 | − | − | − | − | − | − | − | − | − | − | − |
| 60 | − | − | − | − | − | − | − | − | − | − | − |
| 40 | − | − | − | − | − | − | − | − | − | − | + |
| 30 | − | − | − | − | − | − | − | − | − | − | + |
| 20 | − | − | − | − | − | − | − | − | − | + | + |
| 15 | − | − | − | − | − | − | − | − | − | + | + |
| 10 | − | − | − | − | − | − | − | − | − | + | + |
| 0 | − | − | − | − | − | − | − | + | + | + | + |

The synergism which is present is shown in the form of figures using the calculations of the synergistic index shown in table II. The synergistic index is calculated by the method of F. C. Kull et al., Applied Microbiology, vol. 9 (1961), p. 538. Here, the synergistic index is calculated using the following formula:

$$\text{Synergistic index } SI = Q_a/Q_A + Q_b/Q_B.$$

When applying this formula to the biocide system tested in the present context, the parameters in the formula have the following meanings:
$Q_a$=MIT concentration MIT/HCHO biocide mixture
$Q_A$=concentration of MIT as the only biocide
$Q_b$=HCHO concentration in the MIT/HCHO biocide mixture
$Q_B$=concentration of HCHO as the only biocide.

If the synergistic index has a value of above 1, this means that antagonism is present. If the synergistic index assumes a value of 1, this means that an additive effect of the two biocides exists. If the synergistic index assumes a value of less than 1, this means that synergism of the two biocides exists.

TABLE II

*Pseudomonas aeruginosa*: calculation of the
synergistic index of MIT + HCHO
at an incubation time of 96 h/25° C.

| MIC at | | Total | Concentration | | | | SynerGistic |
|---|---|---|---|---|---|---|---|
| MIT concentration $Q_a$ (ppm) | HCHO concentration $Q_b$ (ppm) | concentration of MIT + HCHO $Q_a + Q_b$ (ppm) | MIT (% by weight) | HCHO (% by weight) | $Q_a/Q_A$ | $Q_b/Q_B$ | Index $Q_a/Q_A + Q_b/Q_B$ |
| 0 | 100 | 100 | 0.0 | 100.0 | 0.00 | 1.00 | 1.00 |
| 10 | 75 | 85 | 11.8 | 88.2 | 0.17 | 0.75 | 0.92 |
| 10 | 50 | 60 | 16.7 | 83.3 | 0.17 | 0.50 | 0.67 |
| 15 | 50 | 65 | 23.1 | 76.9 | 0.25 | 0.50 | 0.75 |
| 20 | 50 | 70 | 28.6 | 71.4 | 0.33 | 0.50 | 0.83 |
| 30 | 25 | 55 | 54.5 | 45.5 | 0.50 | 0.25 | 0.75 |
| 40 | 25 | 65 | 61.5 | 38.5 | 0.67 | 0.25 | 0.92 |
| 60 | 0 | 60 | 100.0 | 0.0 | 1.00 | 0.00 | 1.00 |

It can be seen from table II that the optimal synergism, i.e. the lowest synergistic index (0.67), of an MIT/HCHO mixture is obtained with a mixture of 16.7% by weight of MIT and 83.3% by weight of HCHO.

EXAMPLE 2

Analogously to example 1, the synergism of MIT and BNP was shown with regard to the microorganism *Pseudomonas aeruginosa*.

Again, the experimental batches contained a Müller-Hinton broth as the nutrient medium. The cell density was $10^6$ cells/ml. The incubation time was 72 hours at 25° C. Each sample was incubated in a shaker-incubator at 120 rpm.

The MIC values of the biocide composition tested can be seen from table III which follows. The MIC value was 40 ppm when only MIT was employed and 20 ppm when only BNP was employed.

TABLE III

*Pseudomonas aeruginosa*: MIC values of MIT + BNP
at an incubation time of 72 h/25° C.

| MIT concentration (ppm) | BNP concentration (ppm) | | | | | | | |
|---|---|---|---|---|---|---|---|---|
| | 50 | 40 | 30 | 20 | 15 | 10 | 5 | 0 |
| 60 | − | − | − | − | − | − | − | − |
| 50 | − | − | − | − | − | − | − | − |

TABLE III-continued

*Pseudomonas aeruginosa*: MIC values of MIT + BNP
at an incubation time of 72 h/25° C.

| MIT concentration (ppm) | BNP concentration (ppm) | | | | | | | |
|---|---|---|---|---|---|---|---|---|
| | 50 | 40 | 30 | 20 | 15 | 10 | 5 | 0 |
| 40 | − | − | − | − | − | − | − | − |
| 30 | − | − | − | − | − | − | − | + |
| 20 | − | − | − | − | − | − | − | + |
| 15 | − | − | − | − | − | − | − | + |
| 10 | − | − | − | − | − | − | + | + |
| 5 | − | − | − | − | − | + | + | + |
| 0 | − | − | − | − | + | + | + | + |

Synergism was present when MIT and BNP were employed simultaneously. The calculation of the synergistic index can be seen from table IV. Accordingly, the lowest synergistic index for *Pseudomonas aeruginosa* (0.63) was found for a mixture of 75.0% by weight of MIT and 25% by weight of BNP.

TABLE IV

*Pseudomonas aeruginosa*: calculation of the
synergistic index of MIT + BNP
at an incubation time of 72 h/25° C.

| MIC at | | Total | Concentration | | | | Synergistic |
|---|---|---|---|---|---|---|---|
| MIT concentration $Q_a$ (ppm) | BNP concentration $Q_b$ (ppm) | concentration of MIT + BNP $Q_a + Q_b$ (ppm) | MIT (% by weight) | BNP (% by weight) | $Q_a/Q_A$ | $Q_b/Q_B$ | Index $Q_a/Q_A + Q_b/Q_B$ |
| 0 | 20 | 20 | 0.0 | 100.0 | 0.00 | 1.00 | 1.00 |
| 5 | 15 | 20 | 25.0 | 75.0 | 0.13 | 0.75 | 0.88 |
| 10 | 10 | 20 | 50.0 | 50.0 | 0.25 | 0.50 | 0.75 |
| 15 | 5 | 20 | 75.0 | 25.0 | 0.38 | 0.25 | 0.63 |
| 20 | 5 | 25 | 80.0 | 20.0 | 0.50 | 0.25 | 0.75 |
| 40 | 0 | 40 | 100.0 | 0.0 | 1.00 | 0.00 | 1.00 |

EXAMPLE 3

Analogously to example 1, the synergism of MIT and PMG is shown with regard to the microorganism *Pseudomonas aeruginosa*.

Again, the experimental batches contained a Müller-Hinton broth as the nutrient medium. The cell density was $10^6$ cells/ml. The incubation time was 48 hours at 25° C. Each sample was incubated in a shaker-incubator at 120 rpm.

The MIC values of the biocide compositions tested can be seen from table V which follows. The MIC value was 40 ppm when only MIT was employed and 30 ppm when only PMG was employed.

TABLE V

*Pseudomonas aeruginosa*: MIC values of MIT + PGM at an incubation time of 48 h/25° C.

| MIT concentration (ppm) | PMG concentration (ppm) | | | | | | | |
|---|---|---|---|---|---|---|---|---|
| | 100 | 75 | 50 | 40 | 30 | 20 | 10 | 0 |
| 50 | − | − | − | − | − | − | − | − |
| 40 | − | − | − | − | − | − | − | − |
| 30 | − | − | − | − | − | − | − | + |
| 20 | − | − | − | − | − | − | − | + |
| 15 | − | − | − | − | − | − | − | + |
| 10 | − | − | − | − | − | − | − | + |
| 7.5 | − | − | − | − | − | − | − | + |
| 5 | − | − | − | − | − | − | − | + |
| 0 | − | − | − | − | − | + | + | + |

Synergism was present when MIT and PMG were employed simultaneously. The calculation of the synergistic index can be seen from table VI. Accordingly, the lowest synergistic index (0.46) for *Pseudomonas aeruginosa* was found for a mixture of 33.3% by weight of MIT and 66.7% by weight of PMG.

TABLE VI

*Pseudomonas aeruginosa*: calculation of the synergism of MIT + PMG at an incubation time of 48 h/25° C.

| MIC at MIT concentration $Q_a$ (ppm) | MIC at PMG concentration $Q_b$ (ppm) | Total concentration MIT + PMG $Q_a + Q_b$ (ppm) | Concentration MIT (% by weight) | Concentration PMG (% by weight) | $Q_a/Q_A$ | $Q_b/Q_B$ | Synergistic index $Q_a/Q_A + Q_b/Q_B$ |
|---|---|---|---|---|---|---|---|
| 0 | 30 | 30 | 0.0 | 100.0 | 0.00 | 1.00 | 1.00 |
| 5 | 20 | 25 | 20.0 | 80.0 | 0.13 | 0.67 | 0.79 |
| 5 | 10 | 15 | 33.3 | 66.7 | 0.13 | 0.33 | 0.46 |
| 7.5 | 10 | 17.5 | 42.9 | 57.1 | 0.19 | 0.33 | 0.52 |
| 10 | 10 | 20 | 50.0 | 50.0 | 0.25 | 0.33 | 0.58 |
| 15 | 10 | 25 | 60.0 | 40.0 | 0.38 | 0.33 | 0.71 |
| 20 | 10 | 30 | 66.7 | 33.3 | 0.50 | 0.33 | 0.83 |
| 40 | 0 | 40 | 100.0 | 0.0 | 1.00 | 0.00 | 1.00 |

EXAMPLE 4

Analogously to example 1, the synergism of MIT and OPP was shown with regard to the microorganism *Pseudomonas aeruginosa*.

Again, the experimental batches contained a Müller-Hinton broth as the nutrient medium. The cell density was $10^6$ cells/ml. The incubation time was 72 hours at 25° C. Each sample was incubated in a shaker-incubator at 120 rpm.

The MIC values of the biocide composition tested can be seen from table VII which follows. The MIC value was 40 ppm when only MIT was employed and 750 ppm when only OPP was employed.

TABLE VII

*Pseudomonas aeruginosa*: MIC values of MIT + OPP at an incubation time of 72 h/25° C.

| MIT concentration (ppm) | OPP concentration (ppm) | | | | | | | | | |
|---|---|---|---|---|---|---|---|---|---|---|
| | 750 | 500 | 375 | 250 | 200 | 150 | 50 | 37.5 | 25 | 12.5 | 0 |
| 50 | − | − | − | − | − | − | − | − | − | − |
| 40 | − | − | − | − | − | − | − | − | − | − |

TABLE VII-continued

*Pseudomonas aeruginosa*:
MIC values of MIT + OPP at an incubation time of 72 h/25° C.

| MIT concentration | OPP concentration (ppm) | | | | | | | | | | |
|---|---|---|---|---|---|---|---|---|---|---|---|
| (ppm) | 750 | 500 | 375 | 250 | 200 | 150 | 50 | 37.5 | 25 | 12.5 | 0 |
| 30 | − | − | − | − | − | − | + | + | + | + | + |
| 25 | − | − | − | − | − | − | + | + | + | + | + |
| 20 | − | − | − | − | − | − | + | + | + | + | + |
| 15 | − | − | − | − | − | − | + | + | + | + | + |
| 12.5 | − | − | − | − | − | + | + | + | + | + | + |
| 10 | − | − | − | − | − | + | + | + | + | + | + |
| 7.5 | − | − | − | − | + | + | + | + | + | + | + |
| 5 | − | − | + | + | + | + | + | + | + | + | + |
| 2.5 | − | − | + | + | + | + | + | + | + | + | + |
| 0 | − | + | + | + | + | + | + | + | + | + | + |

Synergism was present when MIT and OPP were employed simultaneously. The calculation of the synergistic index can be seen from table VIII. Accordingly, the lowest synergistic index (0.52) for *Pseudomonas aeruginosa* was found for a mixture of from 2.9 to 4.8% by weight of MIT and from 97.1 to 95.2% by weight of OPP.

TABLE VIII

*Pseudomonas aeruginosa*:
calculation of the synergism of MIT + OPP
at an incubation time of 72 h/25° C.

| MIC at | | | Concentration | | | | Synergistic |
|---|---|---|---|---|---|---|---|
| MIT concentration $Q_a$ (ppm) | OPP concentration $Q_b$ (ppm) | Total concentration MIT + OPP $Q_a + Q_b$ (ppm) | MIT (% by weight) | OPP (% by weight) | $Q_a/Q_A$ | $Q_b/Q_B$ | index $Q_a/Q_A + Q_b/Q_B$ |
| 0 | 750 | 750 | 0.0 | 100.0 | 0.00 | 1.00 | 1.00 |
| 2.5 | 500 | 502.5 | 0.5 | 99.5 | 0.06 | 0.67 | 0.73 |
| 5 | 500 | 505 | 1.0 | 99.0 | 0.13 | 0.67 | 0.79 |
| 7.5 | 375 | 382.5 | 2.0 | 98.0 | 0.19 | 0.50 | 0.69 |
| 7.5 | 250 | 257.5 | 2.9 | 97.1 | 0.19 | 0.33 | 0.52 |
| 10 | 200 | 210 | 4.8 | 95.2 | 0.25 | 0.27 | 0.52 |
| 12.5 | 200 | 212.5 | 5.9 | 94.1 | 0.31 | 0.27 | 0.58 |
| 15 | 150 | 165 | 9.1 | 90.0 | 0.38 | 0.20 | 0.58 |
| 20 | 150 | 170 | 11.8 | 88.2 | 0.50 | 0.20 | 0.70 |
| 25 | 150 | 175 | 14.3 | 85.7 | 0.63 | 0.20 | 0.83 |
| 40 | 0 | 40 | 100.0 | 0.0 | 1.00 | 0.00 | 1.00 |

EXAMPLE 5

Analogously to example 1, the synergism of MIT and ZnPy was shown with regard to the microorganism *Pseudomonas aeruginosa*.

Again, the experimental batches contained a Müller-Hinton broth as the nutrient medium. The cell density was $10^6$ cells/ml. The incubation time was 72 hours at 25° C. Each sample was incubated in a shaker-incubator at 120 rpm.

The MIC values of the biocide composition tested can be seen from table IX which follows. The MIC value was 40 ppm when only MIT was employed and over 100 ppm when only ZnPy was employed.

TABLE IX

*Pseudomonas aeruginosa*: MIC values of MIT + ZnPy
at an incubation time of 72 h/25° C.

| MIT concentration | ZnPy concentration (ppm) | | | | | | | |
|---|---|---|---|---|---|---|---|---|
| (ppm) | 100 | 75 | 50 | 40 | 30 | 20 | 10 | 0 |
| 100 | − | − | − | − | − | − | − | − |
| 80 | − | − | − | − | − | − | − | − |
| 60 | − | − | − | − | − | − | − | − |
| 40 | − | − | − | − | − | − | − | − |
| 30 | − | − | − | − | − | − | − | + |
| 20 | − | − | − | − | − | − | − | + |
| 15 | − | − | − | − | − | − | − | + |
| 10 | − | − | − | − | − | − | − | + |
| 0 | + | + | + | + | + | + | + | + |

Synergism was present when MIT and ZnPy were employed simultaneously. The calculation of the synergistic index can be seen from table X. In the case of ZnPy, an MIC value of 100 ppm was used here as the basis for this calculation. Accordingly, the lowest synergistic index (0.35) for *Pseudomonas aeruginosa* was found for a mixture of 50% by weight of MIT and 50% by weight of ZnPy.

TABLE X

*Pseudomonas aeruginosa*:
calculation of the synergism of MIT + ZnPy
at an incubation time of 72 h/25° C.

| MIT concentration $Q_a$ (ppm) | ZnPy concentration $Q_b$ (ppm) | Total concentration MIT + ZnPy $Q_a + Q_b$ (ppm) | MIC at Concentration MIT (% by weight) | ZnPy (% by weight) | $Q_a/Q_A$ | $Q_b/Q_B$ | Synergistic index $Q_a/Q_A + Q_b/Q_B$ |
|---|---|---|---|---|---|---|---|
| 0  | 100 | 100 | 0.0   | 100.0 | 0.00 | 1.00 | 1.00 |
| 10 | 10  | 20  | 50.0  | 50.0  | 0.25 | 0.10 | 0.35 |
| 15 | 10  | 25  | 60.0  | 40.0  | 0.38 | 0.10 | 0.48 |
| 20 | 10  | 30  | 66.7  | 33.3  | 0.50 | 0.10 | 0.60 |
| 30 | 10  | 40  | 75.0  | 25.0  | 0.75 | 0.10 | 0.85 |
| 40 | 0   | 40  | 100.0 | 0.0   | 1.00 | 0.00 | 1.00 |

EXAMPLE 6

Analogously to example 1, the synergism of MIT and NaPy was shown with regard to the microorganism *Pseudomonas aeruginosa*.

Again, the experimental batches contained a Müller-Hinton broth as the nutrient medium. The cell density was $10^6$ cells/ml. The incubation time was 96 hours at 25° C. Each sample was incubated in a shaker-incubator at 120 rpm.

The MIC values of the biocide composition tested can be seen from table XI which follows. The MIC value was 60 ppm when only MIT was employed and 200 ppm when only NaPy was employed.

TABLE XI

*Pseudomonas aeruginosa*: MIC values of MIT + NaPy
at an incubation time of 96 h/25° C.

| MIT concentration (ppm) | NaPy concentration (ppm) | | | | | | | |
|---|---|---|---|---|---|---|---|---|
| | 300 | 200 | 150 | 100 | 75 | 50 | 25 | 0 |
| 100 | − | − | − | − | − | − | − | − |
| 80  | − | − | − | − | − | − | − | − |
| 60  | − | − | − | − | − | − | − | − |
| 40  | − | − | − | − | − | − | + | + |
| 30  | − | − | − | − | − | − | + | + |
| 20  | − | − | − | − | − | + | + | + |
| 15  | − | − | − | − | − | + | + | + |
| 10  | − | − | − | − | + | + | + | + |
| 0   | − | − | + | + | + | + | + | + |

Synergism was present when MIT and NaPy were employed simultaneously. The calculation of the synergistic index can be seen from table XII. Accordingly, the lowest synergistic index (0.63) for *Pseudomonas aeruginosa* was found for a mixture of 16.7% by weight of MIT and 83.3% by weight of NaPy.

TABLE XII

*Pseudomonas aeruginosa*:
calculation of the synergism of MIT + NaPy
at an incubation time of 96 h/25° C.

| MIT concentration $Q_a$ (ppm) | NaPy concentration $Q_b$ ppm) | Total concentration MIT + NaPy $Q_a + Q_b$ (ppm) | MIC at Concentration MIT (% by weight) | NaPy (% by weight) | $Q_a/Q_A$ | $Q_b/Q_B$ | Synergistic index $Q_a/Q_A + Q_b/Q_B$ |
|---|---|---|---|---|---|---|---|
| 0  | 200 | 200 | 0.0  | 100.0 | 0.00 | 1.00 | 1.00 |
| 10 | 150 | 160 | 6.3  | 93.8  | 0.17 | 0.75 | 0.92 |
| 10 | 100 | 110 | 9.1  | 90.9  | 0.17 | 0.50 | 0.67 |
| 15 | 75  | 90  | 16.7 | 83.3  | 0.25 | 0.38 | 0.63 |
| 20 | 75  | 95  | 21.1 | 78.9  | 0.33 | 0.38 | 0.71 |

TABLE XII-continued

*Pseudomonas aeruginosa*:
calculation of the synergism of MIT + NaPy
at an incubation time of 96 h/25° C.

| MIC at | | | | | | | |
|---|---|---|---|---|---|---|---|
| MIT concentration $Q_a$ (ppm) | NaPy concentration $Q_b$ ppm) | Total concentration MIT + NaPy $Q_a + Q_b$ (ppm) | Concentration MIT (% by weight) | NaPy (% by weight) | $Q_a/Q_A$ | $Q_b/Q_B$ | Synergistic index $Q_a/Q_A + Q_b/Q_B$ |
| 30 | 50 | 80 | 37.5 | 62.5 | 0.50 | 0.25 | 0.75 |
| 40 | 50 | 90 | 44.4 | 55.6 | 0.67 | 0.25 | 0.92 |
| 60 | 0 | 60 | 100.0 | 0.0 | 1.00 | 0.00 | 1.00 |

EXAMPLE 7

Analogously to example 1, the synergism of MIT and BBIT was shown with regard to the microorganism *Pseudomonas aeruginosa*.

Again, the experimental batches contained a Müller-Hinton broth as the nutrient medium. The cell density was $10^6$ cells/ml. The incubation time was 72 hours at 25° C. Each sample was incubated in a shaker-incubator at 120 rpm.

The MIC values of the biocide composition tested can be seen from table XIII which follows. The MIC value was 40 ppm when only MIT was employed and over 500 ppm when only BBIT was employed.

TABLE XIII

*Pseudomonas aeruginosa*: MIC values of MIT + BBIT
at an incubation time of 72 h/25° C.

| MIT concentration | BBIT concentration (ppm) | | | | | | | |
|---|---|---|---|---|---|---|---|---|
| (ppm) | 500 | 375 | 250 | 200 | 150 | 100 | 50 | 0 |
| 50 | − | − | − | − | − | − | − | − |
| 40 | − | − | − | − | − | − | − | − |
| 30 | − | − | − | − | − | − | − | + |
| 20 | − | − | − | − | − | − | − | + |
| 15 | − | − | − | − | − | − | − | + |
| 10 | − | − | − | − | − | − | + | + |
| 5 | + | + | + | + | + | + | + | + |
| 0 | + | + | + | + | + | + | + | + |

Synergism was present when MIT and BBIT were employed simultaneously. The calculation of the synergistic index can be seen from table XIV. In the case of BBIT, an MIC of 500 ppm was used here as the basis for this calculation. Accordingly, the lowest synergistic index (0.45) for *Pseudomonas aeruginosa* was found for a mixture of 9.1% by weight of MIT and 90.9% by weight of BBIT.

TABLE XIV

*Pseudomonas aeruginosa*:
calculation of the synergism of MIT + BBIT
at an incubation time of 72 h/25° C.

| MIC at | | | | | | | |
|---|---|---|---|---|---|---|---|
| MIT concentration $Q_a$ (ppm) | BBIT concentration $Q_b$ ppm) | Total concentration MIT + BBIT $Q_a + Q_b$ ppm) | Concentration MIT (% by weight) | BBIT (% by weight) | $Q_a/Q_A$ | $Q_b/Q_B$ | Synergistic index $Q_a/Q_A + Q_b/Q_B$ |
| 0 | 500 | 500 | 0.0 | 100.0 | 0.00 | 1.00 | 1.00 |
| 10 | 100 | 110 | 9.1 | 90.9 | 0.25 | 0.20 | 0.45 |
| 15 | 50 | 65 | 23.1 | 76.9 | 0.38 | 0.10 | 0.48 |
| 20 | 50 | 70 | 28.6 | 71.4 | 0.50 | 0.10 | 0.60 |
| 30 | 50 | 80 | 37.5 | 62.5 | 0.75 | 0.10 | 0.85 |
| 40 | 0 | 40 | 100.5 | 0.0 | 1.00 | 0.00 | 1.00 |

EXAMPLE 8

The synergism of MIT and HMBIT toward the microorganism *Pseudomonas aeruginosa* was demonstrated in a manner similar to that described in example 1.

Again, the experimental batches contained a Müller-Hinton broth as nutrient medium. The cell density was $10^6$ microorganisms/ml. The incubation time was 48 hours at 30° C. Each sample was incubated in a shaker-incubator at 120 rpm.

Table XV hereinbelow shows the MIC values of the biocide composition tested. When MIT is used alone, the MIC value was 50 ppm and when HMBIT was used alone it was 150 ppm.

TABLE XV

*Pseudomonas aeruginosa*: MIC values of MIT + HMBIT at an incubation time of 48 h/30° C.

| MIT concentration (ppm) | HMBIT concentration (ppm) | | | | | | | |
|---|---|---|---|---|---|---|---|---|
| | 180 | 100 | 75 | 50 | 25 | 10 | 5 | 0 |
| 50 | − | − | − | − | − | − | − | − |
| 40 | − | − | − | − | − | − | + | + |
| 30 | − | − | − | − | − | + | + | + |
| 20 | − | − | − | − | + | + | + | + |
| 15 | − | − | − | − | + | + | + | + |
| 10 | − | − | + | + | + | + | + | + |
| 5 | − | − | + | + | + | + | + | + |
| 0 | − | + | + | + | + | + | + | + |

Synergism was present when MIT and HMBIT were employed simultaneously. Calculation of the synergistic index can be seen from table XVI. According to this table, the lowest synergistic index (0.63) for *Pseudomonas aeruginosa* was found for a mixture of 23.1% by weight of MIT and 76.9% by weight of HMBIT.

TABLE XVI

*Pseudomonas aeruginosa*: calculation of the synergism of MIT + HMBIT at an incubation time of 48 h/25° C.

| MIC at | | | Concentration | | | | Synergistic |
|---|---|---|---|---|---|---|---|
| MIT concentration $Q_a$ (ppm) | HMBIT concentration $Q_b$ ppm | Total concentration MIT + HMBIT $Q_a + Q_b$ ppm | MIT (% by weight) | HMBIT (% by weight) | $Q_a/Q_A$ | $Q_b/Q_B$ | index $Q_a/Q_A + Q_b/Q_B$ |
| 0 | 150 | 150 | 0.0 | 100.0 | 0.00 | 1.00 | 1.00 |
| 5 | 100 | 105 | 4.8 | 95.2 | 0.10 | 0.67 | 0.77 |
| 15 | 75 | 90 | 16.7 | 83.3 | 0.30 | 0.50 | 0.80 |
| 15 | 50 | 65 | 23.1 | 76.9 | 0.30 | 0.33 | 0.63 |
| 20 | 50 | 70 | 28.6 | 71.4 | 0.40 | 0.33 | 0.73 |
| 30 | 25 | 55 | 54.5 | 45.5 | 0.60 | 0.17 | 0.77 |
| 40 | 10 | 50 | 80.0 | 20.0 | 0.80 | 0.07 | 0.87 |
| 50 | 0 | 50 | 100.0 | 0.0 | 1.00 | 0.00 | 1.00 |

EXAMPLE 9

The synergism of MIT and BAC toward the microorganism *Pseudomonas aeruginosa* was demonstrated in a manner similar to that described in example 1.

Again, the experimental batches contained a Müller-Hinton broth as nutrient medium. The cell density was $10^6$ microorganisms/ml. The incubation time was 48 hours at 25° C. Each sample was incubated in a shaker-incubator at 120 rpm.

Table XVII hereinbelow shows the MIC values of the biocide composition tested. When MIT is used alone, the MIC value was 40 ppm and when BAC was used alone it was 80 ppm.

TABLE XVII

*Pseudomonas aeruginosa*: MIC values of MIT + BAC at an incubation time of 48 h/25° C.

| MIT concentration (ppm) | BAC concentration (ppm) | | | | | | | | |
|---|---|---|---|---|---|---|---|---|---|
| | 100 | 80 | 60 | 50 | 40 | 30 | 20 | 10 | 0 |
| 60 | − | − | − | − | − | − | − | − | − |
| 50 | − | − | − | − | − | − | − | − | − |
| 40 | − | − | − | − | − | − | − | − | − |
| 30 | − | − | − | − | − | − | − | − | + |
| 20 | − | − | − | − | − | − | − | − | + |
| 15 | − | − | − | − | − | + | + | + | + |
| 10 | − | − | − | − | − | + | + | + | + |
| 5 | − | − | − | − | − | + | + | + | + |
| 0 | − | − | + | + | + | + | + | + | + |

Synergism was present when MIT and BAC were employed simultaneously. Calculation of the synergistic index can be seen from table XVIII. According to this table, the lowest synergistic index (0.63) for *Pseudomonas aeruginosa* was found for a mixture of 11.1% by weight of MIT and 88.9% by weight of BAC and for a mixture of 66.7% by weight of MIT and 33.3% by weight of BAC.

TABLE XVIII

*Pseudomonas aeruginosa*:
calculation of the synergism of MIT + BAC
at an incubation time of 48 h/25° C.

| MIC at | | Total concentration | Concentration | | | | Synergistic |
|---|---|---|---|---|---|---|---|
| MIT concentration $Q_a$ (ppm) | BAC concentration $Q_b$ (ppm) | MIT + BAC $Q_a + Q_b$ ppm | MIT (% by weight) | BAC (% by weight) | $Q_a/Q_A$ | $Q_b/Q_B$ | index $Q_a/Q_A + Q_b/Q_B$ |
| 0  | 80 | 80 | 0.0   | 100.0 | 0.00 | 1.00 | 1.00 |
| 5  | 60 | 65 | 7.7   | 92.3  | 0.13 | 0.75 | 0.88 |
| 5  | 50 | 55 | 9.1   | 90.9  | 0.13 | 0.63 | 0.75 |
| 5  | 40 | 45 | 11.1  | 88.9  | 0.13 | 0.50 | 0.63 |
| 10 | 40 | 50 | 20.0  | 80.0  | 0.25 | 0.50 | 0.75 |
| 15 | 40 | 55 | 27.3  | 72.7  | 0.38 | 0.50 | 0.88 |
| 20 | 30 | 50 | 40.0  | 60.0  | 0.50 | 0.38 | 0.88 |
| 20 | 20 | 40 | 50.0  | 50.0  | 0.50 | 0.25 | 0.75 |
| 20 | 10 | 30 | 66.7  | 33.3  | 0.50 | 0.13 | 0.63 |
| 30 | 10 | 40 | 75.0  | 25.0  | 0.75 | 0.13 | 0.88 |
| 40 | 0  | 40 | 100.0 | 0.0   | 1.00 | 0.00 | 1.00 |

We claim:

1. A synergistic biocide composition, which is substantially free from 5-chloro-2-methylisothiazolin-3-one comprising 2-methylisothiazolin-3-one as biocidal active ingredient wherein the composition comprises zinc pyrithione as further biocidal active ingredient.

2. A biocide composition as claimed in claim 1, wherein the 2-methylisothiazolin-3-one and the zinc pyrithione is present in a weight ratio of 20:80 to 80:20.

3. A biocide composition as claimed in claim 1, wherein the 2-methylisothiazolin-3-one is present in a concentration of from 1 to 50% by weight based on the entire biocide composition.

4. A biocide composition as claimed in claim 1, wherein zinc pyrithione is present in a concentration of from 1 to 50% by weight based on the entire biocide composition.

5. A biocide composition as claimed in claim 1, characterized in that the 2-methylisothiazolin-3-one and the zinc pyrithione is present in a total concentration of from 1 to 100% by weight, based on the entire biocide composition.

6. A biocide composition as claimed in claim 5, wherein the 2-methylisothiazolin-3-one and the zinc pyrithione are present in a total concentration of from 1 to 30% by weight, based on the entire biocide composition.

7. A biocide composition as claimed in claim 1, wherein a polar and/or unpolar liquid medium is/are present.

8. A biocide composition as claimed in claim 7, wherein the polar liquid medium present is water, an alcohol, a glycol, a glycol ether, a glycol ester, a polyethylene glycol, a polypropylene glycol, N,N-dimethylformamide, 2,24-trimethylpentanediol monoisobutyrate or a mixture of at least two of these substances.

9. A biocide composition as claimed in claim 8, wherein the polar liquid medium present is water.

10. A method of controlling harmful microorganisms which comprises contacting said harmful microorganisms with an effective amount of the composition of claim 1.

11. A substance mixture or material, preserved against harmful microorganisms, which comprises an amount of a biocide composition as claimed in claim 1 which is effective to control harmful microorganisms.

12. A biocide composition as claimed in claim 1 wherein zinc pyrithione is present at a ratio of 25-50 wt % and 2-methylisothiazolin-3-one is present at a ratio of 50 wt % to 75 wt % based on the entire biocide composition.

* * * * *